United States Patent [19]

Berg et al.

[11] Patent Number: 4,620,901

[45] Date of Patent: Nov. 4, 1986

[54] SEPARATION OF ACETONE FROM METHANOL BY EXTRACTIVE DISTILLATION

[76] Inventors: Lloyd Berg; Karl J. Warren, both of 1314 S. Third Ave., Bozeman, Mont. 59715

[21] Appl. No.: 794,474

[22] Filed: Nov. 4, 1985

[51] Int. Cl.<sup>4</sup> .................. B01D 3/40; C07C 29/84
[52] U.S. Cl. ........................... 203/51; 203/56; 203/57; 203/60; 203/62; 203/63; 203/64; 568/411
[58] Field of Search .............. 203/60, 51, 56, 57, 203/62–64; 568/411, 913

[56] References Cited

U.S. PATENT DOCUMENTS

| 2,179,991 | 11/1939 | Bright et al. ............... 568/411 |
| 3,419,477 | 12/1968 | Mattia ......................... 568/411 |
| 4,501,645 | 2/1985 | Berg et al. ................... 203/60 |
| 4,543,164 | 9/1985 | Berg et al. ................... 203/60 |

FOREIGN PATENT DOCUMENTS

| 510801 | 3/1955 | Canada ........................ 568/411 |
| 911191 | 7/1946 | France ......................... 203/51 |
| 32788 | 8/1965 | German Democratic Rep. ........................... 568/411 |

*Primary Examiner*—Wilbur Bascomb

[57] ABSTRACT

Acetone cannot be completely removed from acetone-methanol mixtures by distillation because of the presence of the minimum boiling azeotrope. Acetone can be readily separated from methanol by using extractive distillation in which the extractive agent is dimethylformamide, either alone or admixed with other compounds. Typical examples of effective agents are: dimethylformamide; dimethylformamide and diethylene glycol; dimethyl formamide, glycerine and propylene glycol.

2 Claims, No Drawings

SEPARATION OF ACETONE FROM METHANOL BY EXTRACTIVE DISTILLATION

FIELD OF THE INVENTION

This invention relates to a method for separating acetone from methanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Acetone and methanol are two of the most widely used solvents and mixtures of these two occur with great frequency. The usual method of recovering volatile solvents is by rectification in a multiplate column. However in this case, complete recovery by rectification is impossible due to the formation of the minimum azeotrope between these two. Acetone, b.p. 56.1° C. and methanol, b.p 64.5° C. form a minimum azeotrope boiling at 55.7° C. at one atmosphere pressure and containing 88 weight percent acetone, 12 weight percent methanol. As pressure is increased, the azeotrope composition gets richer in methanol, thus 34% at 4.56 Atm., 46% at 7.82 Atm. and 56% at 11.6 Atm. It is therefore impossible to produce pure acetone from acetone-methanol mixtures by rectification because the lower boiling azeotrope will always come off overhead as the initial product. Any mixture of acetone and methanol subjected to rectification at one atmosphere pressure will produce an overhead product boiling at 55.7° C. and containing 88% acetone, 12% methanol.

Extractive distillation would be an attractive method of effecting the separation of acetone from methanol if agents can be found that (1) will break the acetone-methanol azeotrope and (2) are easy to recover from the methanol, that is form no azeotrope with methanol and boil sufficiently above methanol to make the separation by rectification possible with only a few theoretical plates.

Extractive distillation typically requires the addition of an equal amount to twice as much extractive agent as the acetone-methanol on each plate in the rectification column. The extractive agent should be heated to about the same temperature as the plate into which it is introduced. Thus extractive distillation imposes and additional heat requirement on the column as well as somewhat larger plates. However this is less than the increase occasioned by the additional agents required in azeotropic distillation.

Another consideration in the selection of the extractive distillation agent is its recovery in the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with methanol otherwise it will form a two phase azeotrope with the methanol in the recovery column and some other method of separation will have to be employed.

The breaking of an azeotrope by extractive distillation is a new concept. The closest application of this concept might be the breaking of the ethanol-water azeotrope. J. Schneible, U.S. Pat. No. 1,469,447 used glycerol, P. V. Smith and C. S. Carlson, U.S. Pat. No. 2,559,519 employed ethoxyethanol and butoxyethanol for this purpose and W. E. Catterall, U.S. Pat. No. 2,591,672 reported gasoline as being effective. These are dehydrations and operate more conventionally as a solvent extraction process rather than an extractive distillation.

OBJECTIVE OF THE INVENTION

The object of this invention is to provide a process or method of extractive distillation that will enhance the relative volatility of acetone from methanol in their separation in a rectification column. It is a further object of this invention to identify suitable extractive distillation agents which will eliminate the acetone-methanol binary azeotrope and make possible the production of pure acetone and methanol by rectification. It is a further object of this invention to identify organic compounds which, in addition to the above constraints, are stable, can be separated from methanol by rectification with relatively few plates and can be recycled to the extractive distillation column and reused with little decomposition.

SUMMARY OF THE INVENTION

The objects of this invention are provided by a process for separating acetone from methanol which entails the use of certain oxygenated, nitrogenous and/or sulfur containing organic compounds as the agent in extractive distillation.

DETAILED DESCRIPTION OF THE INVENTION

We have discovered that dimethylformamide (DMFA), individually but principally in mixtures, will effectively negate the acetone-methanol minimum azeotrope and permit the separation of pure acetone from methanol by rectification when employed as the agent in extractive distillation. Table 1 lists the compounds, mixtures and approximate proportions that we have found to be effective. The data in Table 1 was obtained in a vapor-liquid equilibrium still. In each case, the starting material was the acetone-methanol azeotrope. The ratios are the parts of extractive agent used per part of acetone-methanol azeotrope. The relative volatilities are listed for each of the two ratios employed.

The compounds that are effective as extractive distillation agents when used as mixtures with DMFA are propylene glycol, diethylene glycol, glycerine, butoxypropanol, dimethylsulfoxide, ethyl acetoacetate, Cellosolve acetate, glycerol triacetate, methyl n-propyl ketone, ethyl butyl ketone, 4-methoxy-4-methyl pentanone-2, acetophenone, diisobutyl phthalate, dioctyl phthalate, diisooctyl phthalate, diisodecyl phthalate and dipropylene glycol methyl ether.

The ratios shown in Table 1 are the parts of extractive agent used per part of acetone-methanol azeotrope. The two relative volatilities correspond to the two different ratios. For example in Table 1, one part of DMFA with one part of acetone-methanol azeotrope gives a relative volatility of 1.64, 6/5 parts of DMFA give 1.36. One half part of DMFA mixed with one half part of ethyl butyl ketone with one part of acetone-methanol azeotrope gives a relative volatility of 2.29, 3/5 parts of DMFA plus 3/5 parts of ethyl butyl ketone gives 2.37.

TABLE 1

Extractive Distillation Agents Which Are Effective In Separating Acetone From Methanol

| Compounds | Ratios | | Relative Volatility | |
|---|---|---|---|---|
| Dimethylformamide (DMFA) | 1 | 6/5 | 1.64 | 1.36 |
| DMFA, Dimethylsulfoxide | $(1/2)^2$ | $(3/5)^2$ | 1.94 | |
| DMFA, Ethylacetoacetate | " | " | 1.48 | |
| DMFA, Acetophenone | " | " | 1.29 | |
| DMFA, Ethyl butyl ketone | " | " | 2.29 | 2.37 |
| DMFA, 4-Methoxy-4-methylpenta-none-2 | " | " | 1.60 | 1.86 |
| DMFA, Cellosolve acetate | " | " | 1.28 | 1.28 |
| DMFA, Glycerol triacetate | " | " | 1.37 | 1.46 |
| DMFA, Butoxypropanol | " | " | 1.47 | 1.41 |
| DMFA, Diethylene glycol | " | " | 1.86 | 1.85 |
| DMFA, Diisooctyl phthalate | " | " | 1.41 | 1.25 |
| DMFA, Methyl n-propyl ketone | " | " | 1.25 | 1.50 |
| DMFA, Dioctyl phthalate | " | " | 1.12 | 1.27 |
| DMFA, Dipropylene glycol methyl ether | " | " | 1.53 | 2.08 |
| DMFA, Glycerine | " | " | 1.96 | 1.99 |
| DMFA, Glycerine, Propylene glycol | $(1/3)^3$ | $(2/5)^3$ | 2.08 | 2.03 |
| DMFA, Glycerine, Diisobutyl phthalate | " | " | 1.65 | 1.50 |
| DMFA, Glycerine, Dioctyl phthalate | " | " | 1.76 | 1.72 |
| DMFA, Glycerine, Diisodecyl phthalate | " | " | 1.73 | 1.89 |

TABLE 2

Data From Runs Made In Rectification Column

| Extractive Agent(s) | Overhead-% Acetone | Bottoms-% Acetone | Relative Volatility |
|---|---|---|---|
| Dimethylformamide (DMFA) | 70.8 | 15 | 1.79 |
| Dimethylformamide (DMFA) | 73.8 | 15 | 1.85 |
| DMFA | 81.5 | 50 | 1.39 |
| DMFA | 92.4 | 50 | 1.74 |
| 50% DMFA, 50% Diethylene glycol | 98.5 | 50 | 2.54 |
| 50% DMFA, 50% Diethylene glycol | 97.1 | 50 | 2.19 |
| 50% DMFA, 50% Diethylene glycol | 94.2 | 30 | 2.24 |
| 50% DMFA, 50% Diethylene glycol | 93.7 | 30 | 2.20 |

One third parts of DMFA plus 1/3 parts of glycerine plus 1/3 parts of propylene glycol mixed with one part of acetone-methanol azeotrope gives a relative volatility of 2.08., with 2/5 parts, these three give 2.03.

In the examples in Table 1, the starting material is the acetone-methanol azeotrope which possesses a relative volatility of 1.00.

Two of the compounds and mixtures listed in Table 1 and whose relative volatility had been determined in the vapor-liquid equilibrium still, were then evaluated in a glass perforated plate rectification column possessing 4.5 theoretical plates. The results are listed in Table 2. The acetone-methanol azeotrope contains 88% acetone, 12% methanol. In every case the feed or bottoms composition contained less acetone than 88% and in all except the first case, the overhead is richer than 88% acetone. Without the extractive agent, the overhead would approach but not exceed the azeotrope, 88% acetone. This proves that the extractive agent is negating the azeotrope and makes the rectification proceed as if the azeotrope no longer existed. The data in Table 2 was obtained in the following manner. The first line is the result obtained after one hour of operation with one to two parts of extractive agent per part of acetone-methanol being boiled up to the condenser. The second line is the result after 1.5 hours which is usually the maximum time required for the equipment to come to equilibrium. Where the same extractive agent is repeated in Table 2, these indicate the runs in which the agent was recovered and recycled, this to demonstrate its stability and ability to be recycled with no adverse effect.

THE USEFULNESS OF THE INVENTION

The usefulness or utility of this invention can be demonstrated by referring to the data presented in Tables 1 and 2. All of the successful extractive distillation agents show that acetone can be removed from its binary minimum azeotrope with methanol by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity acetone from any mixture with methanol including the minimum azeotrope. The stability of the compounds used and the boiling point difference is such that complete recovery and recycle is obtainable by a simple distillation and the amount required for make-up is small.

WORKING EXAMPLES

Example 1

Thirty grams of acetone, 30 grams of methanol and fifty grams of dimethylformamide (DMFA) were charged to an Othmer type glass vapor-liquid equilibrium still and refluxed for eleven hours. Analysis of the vapor and liquid by gas chromatography gave a vapor composition of 66.3% acetone, 33.7% methanol; a liquid of 54.5% acetone, 45.5% methanol. This indicates a relative volatility of 1.64. Ten grams of DMFA were added and refluxing continued for another nine hours. Analysis indicated a vapor composition of 79% acetone, 21% methanol; a liquid composition of 73.6% acetone, 26.4% methanol which is relative volatility of 1.36.

Example 2

The acetone-methanol azeotrope is 88% acetone, 12% methanol. Fifty grams of the acetone-methanol azeotrope, 25 grams of DMFA and 25 grams of ethyl butyl ketone were charged to the vapor-liquid equilibrium still and refluxed for eleven hours. Analysis indicated a vapor composition of 92.3% acetone, 7.7% methanol; a liquid composition of 83.9% acetone, 16.1% methanol which is a relative volatility of 2.29. Five grams of DMFA and five grams of ethyl butyl ketone were added and refluxing continued for another twelve hours. Analysis indicated a vapor composition of 94.3% acetone, 5.7% methanol; a liquid composition of 85.7% acetone, 14.3% methanol which is a relative volatility of 2.37.

Example 3

Fifty grams of acetone-methanol azeotrope, 17 grams of DMFA, 17 grams of glycerine and 17 grams of propylene glycol were charged to the vapor-liquid equilibrium still and refluxed for eleven hours. Analysis indicated a vapor composition of 89.6% acetone, 10.6% methanol; a liquid composition of 80.5% acetone, 19.5% methanol which is a relative volatility of 2.08. Three grams each of DMFA, glycerine and propylene glycol were added and refluxing continued for another twelve hours. Analysis indicated a vapor composition of 89.2% acetone, 10.8% methanol; a liquid composition of 80.4% acetone, 19.6% methanol which is a relative volatility of 2.02.

Example 4

A glass perforated plate rectification column was calibrated with ethylbenzene and p-xylene which possesses a relative volatility of 1.06 and found to have 4.5 theoretical plates. A solution of 200 grams of methanol and 200 grams of acetone was placed in the stillpot and heated. When refluxing began, an extractive agent comprising pure DMFA was pumped into the column at a rate of 22-23 ml./min. The temperature of the extractive agent as it entered the column was 46° C. After establishing the feed rate of the extractive agent, the heat input to the acetone and methanol in the stillpot was adjusted to give a reflux rate of 10-20 ml./min. After one hour of operation, overhead and bottoms samples of approximately two ml. were collected and analysed by gas chromatography. The overhead analysis was 81.5% acetone, 18.5% methanol. The bottoms analysis ananlysis was 50% acetone, 50% methanol. Using these compositions in the Fenske equation, with the number of theoretical plates in the column being 4.5, gave an average relative volatility of 1.39 for each theoretical plate. After 1.5 hours of total operating time, the overhead and bottoms samples were again taken and analysed. The overhead composition was 92.4% acetone, 7.6% methanol and the bottoms composition was 50% acetone, 50% methanol. This gave an average relative volatility of 1.74 for each theoretical plate.

Example 5

A solution of 200 grams of methanol and 200 grams of acetone was placed in the stillpot of the same column used in Example 4 and heat applied. When refluxing began, an extractive agent comprising 50% DMFA and 50% diethylene glycol was fed to the top of the column at a feed rate of 22-23 ml./min. and a temperature of 46° C. After establishing the feed rate of the extractive agent, the heat input to the acetone and methanol in the stillpot was adjusted to give a total reflux rate of 10-20 ml./min. Having established the reflux rate, the column was allowed to operate for one hour. After one hour of steady operation, overhead and bottoms samples of approximately two ml. were collected and analysed by gas chromatography. The overhead composition was 98.5% acetone, 1.5% methanol; the bottoms composition was 50% acetone, 50% methanol. Using these compositions in the Fenske equation with the number of theoretical plates in the column being 4.5, gave an average relative volatility of 2.54 for each theoretical plate. After 1.5 hours of total operating time, the overhead composition was 97.1% acetone, 2.9% methanol and the bottoms composition was 50% acetone, 50% methanol. This gave an average relative volatility of 2.19 for each theoretical plate.

We have shown that by the use of dimethylformamide, either singly or in combination with other compounds as agents, acetone can be effectively removed from its mixture with methanol in any proportion including the minimum azeotrope.

The nature of the present invention having been described, what we wish to claim as new and useful and secure by Letters Patent is:

1. A method for recovering acetone from a mixture of acetone and methanol which comprises distilling a mixture of acetone and methanol in a rectification column in the presence of about one to two parts of extractive agent per part of acetone-methanol mixture, recovering essentially pure acetone as overhead product and obtaining the extractive agent and methanol from the stillpot, the extractive agent comprises at least dimethylformamide.

2. The method of claim 1 in which the extractive agent comprises a mixture of dimethylformamide and at least one material from the group consisting of propylene glycol, diethylene glycol, glycerine, butoxypropanol, dimethylsulfoxide, ethyl acetoacetate, Cellosolve acetate, glycerol triacetate, methyl n-propyl ketone, ethyl butyl ketone, 4-methoxy-4-methyl pentanone-2, acetophenone, diisobutyl phthalate, dioctyl phthalate, diisooctyl phthalate, diisodecyl phthalate and dipropylene glycol methyl ether.

* * * * *